United States Patent [19]

Banks et al.

[11] Patent Number: 4,689,406

[45] Date of Patent: Aug. 25, 1987

[54] ENHANCEMENT OF MICROBIAL EXPRESSION OF POLYPEPTIDES

[75] Inventors: Allen R. Banks; David L. Hare, both of Boulder, Colo.

[73] Assignee: Amgen, Thousand Oaks, Calif.

[21] Appl. No.: 521,959

[22] Filed: Aug. 10, 1983

[51] Int. Cl.$^4$ .............. C12P 21/00; C12N 15/00; C07H 15/12

[52] U.S. Cl. .............. 536/27; 435/68; 435/172.3; 935/31; 935/42

[58] Field of Search .............. 435/68, 70, 71, 91, 435/172, 317; 536/27

[56] References Cited

FOREIGN PATENT DOCUMENTS 0046039 2/1982 European Pat. Off. .......... 435/172

OTHER PUBLICATIONS

Bujard et al., *Promotors: Structure and Function* (R. Rodriguez, M. Chamberlin, editors) 1982, pp. 121–140.
Gentz et al., "Cloning & Analysis of Strong Promotors is Made Possible by the Downstream Placement of an RNA Termination Signal", PNAS-USA-78(8), 4936–40, 1981.
Bujard, H. "Interaction of E. coli. RNA Polymerase with Promotors", TIBS(5)274–278, Oct. 1980.
Rommens et al., "Gene Expression: Chemical Synthesis & Molecular Cloning of a T5 Early Promotor", Nucleic Acids Research 11(17) 5921–40, 1983.
Sutcliff et al., "Plasmid Cloning Vectors": Chap. 4 in Genetic Engineering, edited by A. Chakrabarty, CRC Press, Inc., Fla., 1978.
Von Gabain et al., "Interaction of E. coli: RNA Polymerase w/Promotors of Corphage & Plasmid DNAS", PNAS VSA 76(1), 189–193, Jan. 1979.

*Primary Examiner*—Thomas G. Wiseman
*Assistant Examiner*—Robin Lyn Teskin
*Attorney, Agent, or Firm*—Marshall, O'Toole, Gerstein, Murray & Bicknell

[57] ABSTRACT

Disclosed are novel DNA sequences operative as promoters of microbial transcription of structural genes and comprising synthetic *E.coli* bacteriophage T5 "early" promoter replica DNA sequences. Disclosed also are novel promoter/operator DNA sequences comprising a synthetic T5 early promoter replica DNA sequence associated with a regulatable operator DNA sequence providing for selectively regulatable transcription of structural genes in, e.g., *E.coli* cells transformed with a DNA vector including same.

1 Claim, No Drawings

ENHANCEMENT OF MICROBIAL EXPRESSION OF POLYPEPTIDES

BACKGROUND

The present invention relates generally to the manipulation of genetic materials and more particularly to the manufacture of DNA sequences facilitating microbial expression of selected plasmid-borne structural genes.

Transcription is the process whereby genetic information stored in deoxyribonucleic acid polymers (DNA) in the cells is transferred or transcribed into ribonucleic acid polymers called messenger RNAs (mRNAs) which are thereafter translated into proteins. The transcription process is initiated by genetic regulatory regions called promoters which effect interaction of a transcribing enzyme (RNA polymerase) and template, thus controlling the level of transcription activity of adjacent nucleotide sequences. Promoters, which usually preceed protein-coding nucleotide sequences ("structural genes") in a DNA polymer, vary in "strength", depending upon their varied abilities to recognize and bind RNA polymerase in a manner facilitating initiation of mRNA transcription.

Regulation of transcription of certan nucleotide sequences in procaryotic organisms is, in many cases, facilitated by nucleotide sequences called operators. Positioned adjacent to, or interwoven with, the promoter, operator sequences generally function through recognition of modulator proteins. Interaction of the operator DNA sequence with a modulator protein (usually an inducible or repressible enzyme) either activates or represses the associated promoter's transcriptional activities, depending upon the nature of the interaction. It is hypothesized that interaction of the modulator protein with the operator alters the affinity of the promoter sequence for RNA polymerase and/or sterically alters access of RNA polymerase to the promoter sequence.

At least two major factors are therefore responsible for controlling the ability of RNA polymerase to interact with the promoter and thereby effect its transcriptional activity: (1) the inherent strength of the promoter, and (2) the state of regulation which may be imposed upon the promoter by an associated operator sequence interacting with the modulator protein. Sequences which precede a selected gene or series of genes in a functional DNA sequence and which operate to determine whether the transcription and eventual expression of a gene will take place are then collectively referred to as promoter/regulator, promoter/operator, or control DNA sequences.

DNA sequences which follow a gene in a DNA polymer and provide a signal for termination of the transcription into messenger RNA are also significant for expression of a gene and are referred to as terminator sequences.

Recombinant DNA methodologies currently enable genetic transformation of a host microorganism with a DNA (plasmid or viral) vector including an exogenous structural gene coding for a polypeptide whose production in the organism is desired Successful expression of an exogenous gene in a transformed host microorganism depends to a great extent on association of the gene in the transformation vector with a suitable promoter/operator sequence so as to insure high level transcription of the gene into mRNA. It is not often the case that the naturally associated promoter/operator of an exogenous gene will allow for high levels of expression in the new host and thus a gene to be microbially expressed must ordinarily be fitted with a new, host-accommodated transcription regulating DNA sequence prior to insertion.

A variety of bacterial and bacteriophage promoters have been studied, particularly in the ubiquitous bacterial host E. coli. In von Gabain, et al., PNAS (USA), 76, pages 189-193 (1979), several E. coli. phage and plasmid DNAs were characterized by the efficiency of the RNA polymerase binding site. The study compared various fragments of the following DNA species: bacterophage T5 fragments A through H, J, K, and M; bacteriophage lambda fragments A–F; bateriophage fd, fragments A and B; bacteriophage T7 intact complete fragment; plasmid pSC101, HINDIII and EcoRI fragments; and plasmid pML21, the entire fragment and fragments A and B. The promoters from the early region of bacteriophage T5 were shown to be the strongest, based upon their ability to complex with or bind RNA polymerase. The T5 HindIII K and N fragments were shown to have rates of complex formation at least ten times greater than the other promoters analyzed in this study.

In other research, promoters from various bacterial and viral sources have been cloned in E. coli and their signal strength in vivo studied using expression from distal promoterless sequences encoding $\beta$-galactosidase or other proteins as an indication of promoter activity [see, Casadaban, M. J., et al., J. Molecular Biology, 138, pages 179-207 (1980); and West, R. W., Jr., et al., Gene, 9, pages 175-193 (1980)]. It is considered likely, based on the above studies, that the T5 promoters, particularly those residing on HindIII restriction fragments K and N, are at least an order of magnitude stronger than any promoters currently in use in recombinant DNA expression systems in E. coli.

The DNA sequences for P25, P26, P28 and P207, promoters which reside on the HindIII N fragment of the T5 viral genome, have been published [see, Bujard, H., TIBS, 5 pages 274-278 1980 and Bujard, H., et al., in Promoters: Structures and Function, (R. Rodriguez, M. Chamberlin, eds.) Praiger, N.Y., pp. 121-140 (1982)]. Gentz, et al. [Gentz, R., PNAS (USA), 78, 4936-4940 (1981)] describes a series of experiments designed to evaluate relative promoter and terminator sequence strengths wherein two marker genes are mounted on a plasmid with a terminator sequence in an intermediate position and wherein provision is made both for incorporation of alternative terminator sequences and for alternative promoter sequences. In one of the plasmid constructions effected, a 212 base pair sequence presumptively including an early T5 promoter (designated P207) was inserted upstream of a promoterless $\beta$-galactosidase gene fragment provided with an fd coliphage transcription terminator sequence at a locus 3' to the protein coding region. Despite the presence of at least a residual portion of the normal lac operator sequence intermediate the promoter and the 62 -galactosidase gene fragment, no mention of potential regulation of T5 promoter function by IPTG "induction" of the lac operator was made.

It is apparent that the T5 bacteriophage promoters could be of significant value in increasing the yield of exogenous proteins expressed in E. coli by recombinant DNA methods, provided that their strength can be harnessed through regulation by either operator sequences or transcription terminator sequences, or, preferably, both. In the absence of such regulation, it is expected that expressing genes under T5 promoter control would be difficult or would unnecessarily tax the metabolic abilities of the cells containing the T5 promoter control gene. Excessive and premature transcription and expression of a selected exogenous gene under T5 promoter control, for example, is likely to disable transformed cell metabolism so that the cells simply would not grow well in culture. Likewise, T5 promoter initiated transcription of DNA sequences beyond the desired protein coding region of a plasmid (e.g., transcribing through and past a structural gene in a circular plasmid) could be highly watseful of cellular energy resources and consequently counterproductive. To date, however, the provision of suitable regulation of T5 promoters in the microbial expression of exogenous polypeptides has not been described.

There thus continues to be a need in the recombinant DNA arts for fully operative methods and materials for enhancing microbial expression of exogenous polypeptides through use of strong promoters such as those extant in the T5 bacteriophage genome in a context permitting appropriate regulation.

BRIEF SUMMARY

Provided according to the present invention are novel synthetic T5 early promoter replica DNA sequences for use in association with plasmid-borne structural genes to secure microbial expression of polypeptides coded for by said structural genes. Replica DNA sequences of the invention in their preferred form comprise double-stranded sequences of nucleotide bases having a length of at least about 30 bases up to about 200 bases and preferably about fifty bases. The following sequence illustrates a presently preferred replica DNA sequence of the invention.

5'-TCATAAAAAT TTTAGTTGCT TAATGCTAAA ATTCTTGATA TAATATTCTC-3'
3'-AGTATTTTTA AAATCAACGA ATTACGATTT TAAGAACTAT ATTATAAGAG-5'

In another of its aspects the present invention provides novel synthetic promoter/operator DNA sequences for use in securing microbial (e.g., *E. coli*) expression of a selected polypeptides coded for by structural genes. Such sequences including a synthetic T5 early promoter replica DNA sequence and one or more selected operator DNA sequences allowing for regulation of promoter function. Preferred operator sequences may be selected from among the group comprising a lac operator, bacteriophage lambda cro operators 1, 2 and/or 3, and *E. coli* ompC or ompF regulatory regions. In its presently most preferred form, a 21-base pair *E. coli* lac operator responsive to isopropylthiogalactoside is employed in the manufacture of synthetic promoter/operator sequences of the invention.

Promoter/operator sequences of the invention may also comprise a DNA sequence of bases the mRNA transcript of which provides a site for binding of the mRNA to ribosomes. The ribosome binding site DNA sequence so provided in its currently most preferred form, comprises an idealized Shine/Dalgarno sequence derived from the ribosome binding site associated with translation of the $C_{II}$ protein of bacteriophage lambda which consists of the following sequence of bases:

5'-TATCTAAGGAAAATACTTACATATGG-3'
Alternative ribosome binding site sequences may include copies of the sequences associated with MS2 coat protein, QB coat protein, lamB, ompF, ompC and trpE.

See, Gold, et al., *Ann. Rev. Microbiol.*, 35, pp. 365–403 (1981).

In other preferred forms of synthetic promoter/operator DNA sequences the promoter and operator base sequences are preceded and/or followed by a sequence of bases comprising a portion of a base sequence which provides a recognition site for restriction endonuclease enzyme cleavage. In addition, whenever possible restriction endonuclease recognition sites may be introduced within the DNA sequence to allow for separation of the operator sequence from the promoter sequence.

The synthetic promoter/operator DNA sequences of the present invention are generally provided 5' to selected structural genes within novel DNA vectors employed to transform selected host cells. In preferred forms of transformation vectors provided by the invention, an mRNA transcription termination DNA sequence is positioned 3' to the selected structural gene. Suitable transcription termination sequences include oop terminator ("Toop"), derived from the bacteriophage lambda genome, and the major fd coliphage terminator. See generally, Adhya, et al., *Ann. Rev. Biochem.*, 47, pp. 967–996 (1978).

Other aspects and advantages of the present invention will be apparent upon consideration of the following detailed description thereof.

DETAILED DESCRIPTION

As employed herein and in the claims, the term "synthetic T5 early promoter replica DNA sequence" shall mean and include a non-naturally-occurring sequence of from 30 to 200 base pairs which substantially includes (i.e., with a frequency of 75 percent or more) base pairs which are positionally homologous within all known early promoter DNA sequences of the T5 viral genome and otherwise substantially includes either the base pair which is most commonly present at any position wherein total homology is absent, or a base which is equally common among such known sequences.

Novel DNA sequences of the invention are preferably synthesized from nucleotide bases according to the method disclosed in the co-owned, co-pending U.S. patent application Ser. No. 375,493, now allowed U.S. Pat. No. 4652639 filed May 6, 1982 by Yitzhak Stabinsky entitled "Manufacture and Expression of Structural Genes". This co-pending application is incorporated by reference herein for the purpose of providing information relating to the method employed in the present invention for manufacturing the claimed DNA sequences.

The following examples illustrate practice of the invention in the design of an exemplary, presently preferred synthetic T5 early promoter replica, the manufacture of the DNA sequences coding for a promoter/operator system and the use of the sequence in vectors and host microorganisms for direct expression of exemplary manufactured genes for urogastrone (EGF) and insulin-like growth factor I (IGF-I).

The following example is directed to the construction of a synthetic T5 early promoter replica DNA sequence.

EXAMPLE 1

A fifty base pair synthetic T5 early promoter replica DNA sequence designated "T5A" was designed based on the currently known sequences of the T5 early promoters, P25, P26, P28, and P207 as reproduced in Table II. See, Bujard, et al., supra. Sequences were analyzed in the regions spanning the base pair at the −50 position to the base at the 0 position. Immediately below the aligned 0 to −50 regions of the "top" strands (5' to 3') of individual naturally-occurring T5 promoter sequences in Table II is a composite sequence, designated as a "Summary" sequence. Where a single base is positionally homologous in all four naturally-occurring sequences, it is listed in the Summary sequence. Where total positional homology does not exist, the Summary sequence lists the base "most commonly" found (i.e., 3 out of 4 occurrences or 2 out of 4 occurrences where three bases are represented at the position). Where there is no "most commonly" found base, bases which are equally common are listed alternatively in the Summary sequence. Below the summary sequence is the top strand of the illustrative T5A replica.

the status of T5A is not expected to change. If, for example, a later-ascertained fifth sequence revealed an adenine at position −40, the thymidine at position −40 in T5A would no longer represent an homologous base but would nonetheless be the most common base at that position.

The following example is directed to the general procedure employed in the synthesis of oligonucleotide fragments for use in the manufacture of a promoter/operator according to the invention.

EXAMPLE 2

Oligonucleotide fragments were synthesized using a three-step procedure and several intermediate washes. Polymer bound dimethoxytrityl protected nucleoside in a sintered glass funnel was first stripped of its 5'-protecting group (dimethoxytrityl) using 2% trichloroacetic acid in dichloromethane for 1½ minutes. The polymer was then washed with methanol, tetrahydrofuran and acetonitrile. The washed polymer was then rinsed with dry acetonitrile, placed under argon and then treated in the condensation step as follows. 0.5 ml of a solution of 10 mg tetrazole in acetonitile was added to the reaction

TABLE II

|  | −50 | −40 | −30 | −20 | −10 |
|---|---|---|---|---|---|
| P25 | TCATAAAAAA | TTTATTTGCT | TTCAGGAAAA | TTTTTCTGTA | TAATAGATTC |
| P26 | ACTTAAAAAT | TTCAGTTGCT | TAATCCTACA | ATTCTTGATA | TAATATTCTC |
| P28 | TAGTTAAAAT | TGTAGTTGCT | AAATGCTTAA | ATACTTGCTA | TAATATTTAT |
| P207 | TTTTAAAAAA | TTCATTTGCT | AAACGCTTCA | AATTCTCGTA | TAATATACTT |
| Summary | TCTTAAAAAT | TTTATTTGCT | TAATGCTAAA | ATTTTTGGTA | TAATATTTTC |
|  | or | or or | or | or | or | or or |
|  | A | C  G | A | TC | C | A  T |
| T5A Replica | TCA<u>TAAAAAT</u> | <u>TTTA</u>G<u>TTGCT</u> | TAATGCTAA<u>A</u> | ATTTTTGAT<u>A</u> | <u>TAATA</u>TTCTC |
|  | −50 | −40 | −30 | −20 | −10 |

In the T5A replica all regions and individual base pairs of the sequences exhibiting total positional homology were conserved. Specifically, the bases in the following positions were conserved: −47; −45 to −42; −40; −37; −35 to −31; −21; and −12 to −6. For ease of illustration, these are underscored in the Table. Where no base was positionally homologous among all four known sequences, the T5A replica incorporates either the most commonly found base [i.e., bases at positions −50, −46, −39, −29, −28, −26, −25, −24, −20, −19, −18, −16, −15, −5, and −2 (which occur 3 out of 4 times) and bases at positions −49, −27 and −14 (which occur 2 out of 4 times where three bases are represented at the position)]. Where there was no "most common" base at given positions (i.e., at positions −41, −38, −36, −30, −23, −22, −17, −4, −3 and −1) one of two equally common bases was selected for incorporation into the T5A replica. In two instances the T5A sequence design does not include either the homologous, the most common or an equally common base. While guanidine is the most common base at position −13, the T5A sequence includes adenine and while thymidine is the most common base at position −48, adenine is incorporated in the T5A sequence. The T5A sequence nonetheless meets the definitional requirements for a replica DNA sequence of the invention because it substantially includes (i.e., in a frequency of 75 percent or more) the homologous, most common or equally common base for any given position.

It should be noted that as more information is gathered concerning the sequences of other T5 promoters, vessel containing polymer. Then 0.5 ml of 30 mg protected nucleoside phosphoramidite in acetonitrile was added. This reaction was agitated and allowed to react for 2 minutes. The reactants were then removed by suction and the polymer rinsed with acetonitrile. This was followed by the oxidation step wherein 1 ml of a solution containing 0.1 molar $I_2$ in 2,6-lutidine/H$_2$O/THF, 1:2:2, was reacted with the polymer bound oligonucleotide chain for 2 minutes, followed by a $CH_3CN$ rinse. Then the cycle began again with a trichloroacetic acid in $CH_2Cl_2$ treatment. The cycle was repeated until the desired oligonucleotide sequence was obtained.

The final oligonucleotide chain was treated with thiophenol, dioxane, triethylamine 1:2:2, or 45 minutes at room temperature. Then, after rinsing with dioxane, methanol and diethylether, the oligonucleotide was cleaved from the polymer with concentrated ammonia at room temperature. After decanting the solution from the polymer, the concentrated ammonia solution was heated at 60° C. for 16 hours in a sealed tube.

Each oligonucleotide solution was then extracted four times with 1-butanol. The solution was loaded into a 20% polyacrylamide 7 molar urea electrophoresis gel and, after running, the appropriate product band was isolated.

The following example specifically illustrates the preparation of a promoter/operator DNA sequence of the invention including the above-noted T5A sequence and an operator sequence duplicative of the operator of a lac promoter/operator.

EXAMPLE 3

Eight specific deoxyoligonucleotides (numbered 1 through 8) were synthesized according to the procedures of Example 2. The oligonucleotide sequences were purified by polyacrylamide gel electrophoresis and were phosphorylated at the 5' ends using ATP and T4 polynucleotide kinase in a standard reaction using one nanomole of DNA, a two fold excess of ATP and 1 unit of T4 kinase in 20 µl of buffer made with 50 mM hydroxyethylpiperazine ethane sulfonic acid, 10 mM $MgCl_2$, 10 mM dithiothreitol, pH 7.6. After reaction, the kinase was destroyed by boiling for 5 minutes. These phosphorylated oligonucleotides in the buffer were then used directly for ligation.

The oligonucleotides in 20 µl standard buffer were combined to form short duplexes. Each duplex was formed by combining two complementary seqeunces in equimolar amounts, boiling the mixture, then slow cooling over a ½ hour period to room temperature. In this way, four duplexes were formed. These four duplexes were combined sequentially, annealing each set of duplexes at 37° C. for 5 minutes until the final structural gene was in a single tube ready for ligation. The oligonucleotide mixture was then made 150 µmolar in ATP and treated with 84 units of T4DNA ligase for 16 hours at 4° C. The fully ligated promoter/operator sequence was then purified by polyacrylamide gel electrophoresis. Table III below illustrates the final assembled promoter/operator sequence.

TABLE III

```
   HindIII
          1                    3
5'-AGCTTCATA AAAATTTTAG TTGCTTAATG CTAAAATTCT TGATATAATA
3'     AGTAT TTTTAAAATC AACGAATTAC GATTTTAAGA ACTATATTAT
               2                    4

5                    7
TTCTCAATTG TGAGCGGATA ACAATTTATC TAAGGAG-3'
AAGAGTTAAC ACTCGCCTAT TGTTAAATAG ATTCCTCCTAG-5'
    6                    8
                                         BamHI
```

Bracketed regions in the DNA sequence indicate the eight separate oligonucleotides initially formed and also designate the intermediate duplexes (e.g., 1 and 2, 3 and 4, etc.).

This 86-base pair promoter/operator sequence contains the T5A replica as described in Example 1 and a 21-base pair lac-operator control sequence. The transcriptional activity of the promoter sequence is thereby minimally modulated approximately 200-fold by lac repressor enzyme. The lac operator sequence is positioned at the expected mRNA start site, as is found in the naturally-occurring lactose operon [see, Dickson, et al., Science, 187, 27–35 (1975)].

The Table III sequence is also provided with a sticky end of a selected restriction endonuclease enzyme recognition site at its 5' end (here, illustratively a HindIII sticky end). At its 3' end, the sequence has a sticky end of a similarly selected restriction endonuclease recognition site (here, illustratively a BamHI sticky end). Thus there is provided a HindIII-BamHI excisable segment for simple insertion into a plasmid vector. It will be understood that one or more entire duplex recognition sites may be provided at each end which would be enzyme-related in the course of insertion in a vector.

The HindIII site also enables the insertion of an additional operator sequence 5' to the T5 promoter/operator sequence, for possible further control of the promoter sequence. The promoter/operator can also be altered to interface with a variety of genes with different restriction sites and/or ribosome binding sites at different distances. Similarly, the operator sequence can be altered to introduce control sequences from other genetic systems, by altering the oligonucleotide fragments constructed in Example 2.

Also present in the Table III sequence is a sequence facilitating the proper binding of transcribed mRNA to ribosomes.

Following the 21 base pair lac operator in the Table III sequence is an idealized Shine-Dalgarno sequence ("$C_{II}$S.D.") as present in $C_{II}$.

Studies have indicated that sequences beyond base position (−50) are involved in RNA polymerase binding [see, Schmitz, A., et al., Nucl. Acid Res., 6, 111 (1979)]. A portion of the sequence post −50 of a strong promoter, such as E. coli ompA [Braun, et al., Nucl. Acids Res., 10, 2367–2378 (1982)] or similar sequences from the T5 promoters may be inserted 5' to the HindIII site to strengthen RNA polymerase binding further.

The following example relates to procedures for construction of an illustrative plasmid vector including a promoter/operator plasmid vector of the present invention and its use in transformation of microbial host cells to secure expression of the polypeptide product, urogastrone.

EXAMPLE 4

A. Construction of Plasmid pADH44

The promoter/operator DNA sequence illustrated in Table III of Example 3 and having HindIII and BamHI sticky ends was inserted into the large fragment of the E. coli cloning vector pBR325 digested with the restriction endonuclease enzymes, HindIII and BamHI. Clones with the promoter/operator sequence designated "T5-4" were characterized by molecular weight sizing of restriction fragments on PAGE and dideoxynucleotide DNA sequencing.

Plasmid vector T5-4 was then digested with BamHI and SalI, thereby excising a small fragment adjacent and 3' to the promoter/operator sequence. A manufactured gene for urogastrone, is the subject of co-owned, co-pending U.S. patent application Ser. No. 486,091 by Allen R. Banks and David L. Hare, entitled "The Manufacture and Expression of Genes for Urogastrone and Polypeptide Analogs Thereof", filed Apr. 25, 1983, and the disclosures thereof specifically incorporated by reference herein. The manufactured gene was inserted into T5-4 and ligated between the BamHI and SalI recognition sites to form plasmid pADH44 having the Table III promoter/operator sequence of the present invention 5' to the polypeptide coding region. When the plasmid was transformed into a bacterial host strain (e.g., *E. coli* JM103), the polypeptide urogastrone was expressed at levels 15 μg/ml by radioreceptor assay of cell supernatant.

B. Construction of Plasmid pADH68

Plasmid ADH44, constructed in Example 4A, contains the polypeptide coding sequence for urogastrone 3' to the promoter/operator sequence of the present invention. 5' to the HindIII restriction endonuclease enzyme recognition site, at which point the T5-lac promoter/operator sequence originates, there is also an EcoRI restriction endonuclease enzyme recognition site. pAHD44 is digested with restriction endonuclease enzymes EcoRI and SalI, whereby the fragment containing promoter/operator and the urogastrone structural gene sequence is excised from the plasmid.

Further manipulations were performed in an attempt to generate an expression vector which would provide for high levels of *E. coli* expression of the desired protein. These manipulations involved use of a plasmid which is the subject of co-owned, co-pending, concurrently-filed U.S. patent application Ser. No. 521,964 now abandoned by Morris, entitled "DNA Vector" the disclosures of which are specifically incorporated by reference herein. Briefly noted, plasmid pCFM414 (ATCC 40076) employed in the construction, includes a temperature-sensitive mutation in the copy control region. Upon transformation with this vector, host cell cultures grown at 34° C. will have a low number of copies of the plasmid. The plasmid copy number increases fifty-fold (i.e., "runs away") within the host cells upon elevation of the culture temperature above 34° C. Growth at 37° C. will ordinarily be lethal to the cells.

The specific manipulations involved in construction of the vector using ATCC 40076 were as follows. Plasmid pCFM414 was digested with restriction endonuclease enzymes EcoRI and XhoI and the large fragment was isolated. The EcoRI/SalI fragment containing the urogastrone gene from pADH44 was then ligated with the large EcoRI/XhoI fragment of pCFM414 to generate plasmid pADH68. While this construction retained an intact EcoRI recognition site, ligation of the complementary sticky ends of the SalI and XhoI did not restore either recognition site. It is also noteworthy that this construction resulted in the placement of the urogastrone structural gene 5' to transcription terminator sequence "Toop" present 3' to the XhoI site in pCFM414. When plasmid pADH68 was transformed into a bacterial host strain, e.g., *E. coli* JM103, the polypeptide urogastrone was expressed at 5 mg/ml as determined by PAGE on whole cells.

The following example relates to procedures for construction of illustrative plasmid vectors including promoter/operator plasmid vector of the present invention for use in transformation of microbial host cells to secure expession of the polypeptide product insulin-like growth factor I.

EXAMPLE 5

Upon association of the manufactured T5Alac promoter/operator sequence within a suitable i E. coli vector plasmid T5-4 described in Example 4A, further manipulations were performed in order to generate an expression vector which would provide for the production in *E. coli* of the polypeptide insulin-like growth factor I. These manipulations involved use of a manufactured DNA sequence for insulin-like growth factor I, which is the subject of co-owned, co-pending, concurrently-filed U.S. patent application Ser. No. 521,966 now abandoned by Banks, et al., entitled "Microbial Expression of Insulin-Like Growth Factors", now abandoned. The disclosures of said application are specifically incorporated by reference herein. A 222-base pair manufactured IGF-I gene having BamHI and SalI sticky ends was inserted into the *E. coli* cloning vector pBR322 digested with BamHI and SalI. Clones with the gene were characterized by polyacrylamide gel electrophoresis to verify the estimated molecular weight for the IGF-I structural gene. The 222-base pair BamHi/-SalI fragment was excised from pBR322 and inserted into single-stranded bacteriophage M13mp8 and M13mp9 replicative form DNA and sequenced. The manufactured gene for IGF-I was excised from the replicative form by treatment with restriction endonucleases BamHI and SalI.

Plasmid pT5-4 was treated with restriction endonucleases BamHI and SalI and bacterial alkaline phosphatase, thereby cleaving the plasmid 3' to the promoter/operator. The excised manufactured IGF-I gene was then inserted into the plasmid between the BamHI and SalI restriction sites and ligated, creating plasmid pT5-4-IGF-I. The insertion of the 222-base pair oligonucleotide of IGF-I in the correct orientation has been verified by restriction enzyme analysis and molecular weight sizing using polyacrylamide gel electrophoresis.

Plasmid pT5-4-IGF-I was transformed into *E. coli* strain JM103 and then grown as described in Example 7 of the aforementioned Banks, et al., U.S. patent application Ser. No. 521,966 now abandoned. Radioimmunoassay results indicated a value of two micrograms per liter of culture at a concentration corresponding to a spectrophotometric reading of 1 at 600 nanometer wavelength, two micrograms per OD liter in whole cells, and less than 0.18 microgram per OD liter at renatured cell pellet material.

Numerous modifications and variations in the practice of the invention are expected to occur to those skilled in the art upon consideration of the foregoing illustrative examples. Consequently, the invention should be considered only as limited to the extent reflected by the appended claims.

What is claimed is:

1. A DNA sequence operable as a promoter of microbial transcription of a protein-coding DNA sequence and comprising the following double-stranded sequence of nucleotide bases:

```
TCATAAAAAT TTTAGTTGCT TAATGCTAAA
AGTATTTTTA AAATCAACGA ATTACGATTT

ATTCTTGATA TAATATTCTC
                    TAAGAACTAT ATTATAAGAG.
```

* * * * *